United States Patent
Ein-Gal

(10) Patent No.: US 7,611,512 B2
(45) Date of Patent: Nov. 3, 2009

(54) INTERLEAVED ARRAY OF BIPOLAR ELECTRODES

(76) Inventor: Moshe Ein-Gal, 30 Azar Street, Ramat Hasharon 47203 (IL)

(*) Notice: Subject to any disclaimer, the term of this patent is extended or adjusted under 35 U.S.C. 154(b) by 333 days.

(21) Appl. No.: 11/247,171

(22) Filed: Oct. 12, 2005

(65) Prior Publication Data

US 2007/0083198 A1    Apr. 12, 2007

(51) Int. Cl.
*A61B 18/18* (2006.01)
(52) U.S. Cl. .......................... 606/50; 606/41
(58) Field of Classification Search .................. 606/41, 606/45–52
See application file for complete search history.

(56) References Cited

U.S. PATENT DOCUMENTS

| | | | | |
|---|---|---|---|---|
| 4,532,924 A | * | 8/1985 | Auth et al. ..................... | 606/50 |
| 5,634,924 A | * | 6/1997 | Turkel et al. ................... | 606/46 |
| 5,849,022 A | * | 12/1998 | Sakashita et al. ............. | 606/174 |
| 6,451,018 B1 | * | 9/2002 | Lands et al. ................... | 606/50 |
| 6,544,262 B2 | * | 4/2003 | Fleischman .................... | 606/41 |
| 6,723,092 B2 | * | 4/2004 | Brown et al. .................. | 606/41 |
| 6,752,806 B2 | * | 6/2004 | Durgin et al. ................. | 606/45 |

* cited by examiner

*Primary Examiner*—Michael Peffley
(74) *Attorney, Agent, or Firm*—Dekel Patent Ltd; David Klein

(57) ABSTRACT

Apparatus including a first electromagnetic energy element that includes protrusions that jut into recesses formed in a second electromagnetic energy element, and a source of electromagnetic energy connected to the first and second electromagnetic energy elements for operating the first and second electromagnetic energy elements as bipolar electrodes. The first and second electromagnetic energy elements may be both formed with protrusions and recesses that interleave with each other.

8 Claims, 2 Drawing Sheets

INTERLEAVED ARRAY OF BIPOLAR ELECTRODES

FIELD OF THE INVENTION

The present invention relates generally to methods and apparatus for applying energy (e.g., RF energy) to tissues, e.g., for tissue coagulation, and particularly to an interleaved array of bipolar electrodes.

BACKGROUND OF THE INVENTION

It is well known in the prior art to apply energy from electrodes to tissues, for various purposes, such as but not limited to, ablation, coagulation, necrosis, etc. For example, RF energy may be applied to pairs of electrodes in a bipolar mode of operation, wherein one of the electrodes is the cathode and the other is the anode.

One of the many uses of RF energy to ablate tissue is in the treatment of benign prostate hyperplasia (BPH). For example, one current technique, known by the commercial name as transurethral needle ablation (TUNA), involves the transurethral application of a medical probe having a pair of monopolar RF needle electrodes at its distal end. The probe is inserted into the urethra and advanced to a position adjacent the prostate. Thereafter, the RF needles are advanced to penetrate the urethral wall and access the prostatic tissue. A RF current is transmitted through each electrode and passes through the tissue to a grounding pad to form a necrotic region which is eventually absorbed by the body. Treating BPH with the TUNA technique is described, for example, in U.S. Pat. No. 5,366,490 to Edwards et al.

The use of RF electromagnetic energy in the thermal treatment of BPH has several limitations. For example, the use of monopolar RF electrodes presents problems in localizing thermal energy within a desired heating pattern within the prostatic tissue. Moreover, the heating patterns generated by the TUNA procedure with the monopolar electrode arrangement are nonsymmetrical. In addition, the flow of RF current from the monopolar electrodes to the grounding pad increases the potential of healthy tissue being subjected to thermal energy and destroyed. Furthermore, the monopolar electrode arrangement of the TUNA instrument is limited with respect to its ability to generate heating patterns of various shapes. Bipolar electrodes have also been used to treat BPH. For example, U.S. Pat. No. 6,016,452 to Kasevich describes a system that incorporates a bipolar or multipolar electrode array to create an electric field where the heat created is confined solely to a specific volume of the prostate gland and therefore the heated tissue is defined only by the electrode geometry. The bipolar electrode array provides a variety of three dimensional, symmetric heating patterns within the prostatic tissue depending on the relative electrode lengths and angular separation. The system provides precision tissue temperature and impedance measurements thereby enabling the surgeon to accurately predict heating pattern performance and tissue response to RF heating.

SUMMARY OF THE INVENTION

The present invention seeks to provide a novel interleaved array of bipolar electrodes for applying energy to tissues, as is described more in detail hereinbelow.

There is thus provided in accordance with an embodiment of the present invention apparatus including a first electromagnetic energy element that includes protrusions that jut into recesses formed in a second electromagnetic energy element, and a source of electromagnetic energy connected to the first and second electromagnetic energy elements for operating the first and second electromagnetic energy elements as bipolar electrodes. The first and second electromagnetic energy elements may be both formed with protrusions and recesses that interleave with each other.

For example, the first and second electromagnetic energy elements may each include an electrically conducting planar member with a serpentine surface that defines the interleaving protrusions and recesses. Alternatively, there may be an array of pins and channels that interleave with each other.

In accordance with an embodiment of the present invention the first and second electromagnetic energy elements may be flexible and bendable. A sensor may be disposed on the first and/or second electromagnetic energy elements (e.g., temperature sensor, pressure sensor, and/or electrical resistance sensor).

In accordance with an embodiment of the present invention, insulating material may be placed on or between portions of said electromagnetic energy elements, such as to provide desired spatial distribution of energy deposition.

In accordance with another embodiment of the present invention, each electromagnetic energy element may be formed by sub-elements operable to be electrically connected to each other, thus changing the shape of said electromagnetic energy element.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
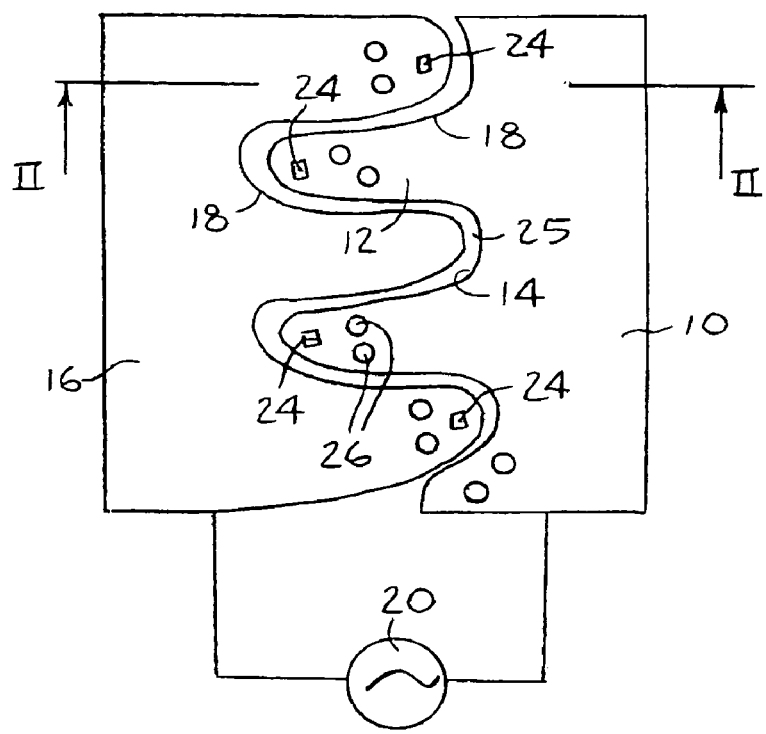
FIG. 1 is a simplified illustration of illustrates apparatus for applying energy to tissues, constructed and operative in accordance with an embodiment of the present invention.

Reference is now made to FIG. 1, which illustrates apparatus for applying energy to tissues, constructed and operative in accordance with an embodiment of the present invention.

The apparatus may include a first electromagnetic energy element 10 that includes protrusions 12 that jut into recesses 14 formed in a second electromagnetic energy element 16. Both first and second electromagnetic energy elements 10 and 16 may be formed with protrusions 12 and recesses 14 that interleave with each other, separated by a gap 25. In the non-limiting illustrated embodiment, the first and second electromagnetic energy elements 10 and 16 each include an electrically conducting planar member, constructed of a medically safe electrically conducting material, such as, but not limited to, metal plate or foil of AISI 316 stainless steel, having a serpentine surface 18 that defines the interleaving protrusions 12 and recesses 14. The serpentine surface 18 may be sinusoidal in shape, semi-circular and the like, but does not have to be arcuate or curvilinear and may alternatively be saw-toothed or other shapes.

A source 20 of electromagnetic energy (e.g., RF generator) may be connected to the first and second electromagnetic energy elements 10 and 16 for operating them as bipolar electrodes.

Figure 3:
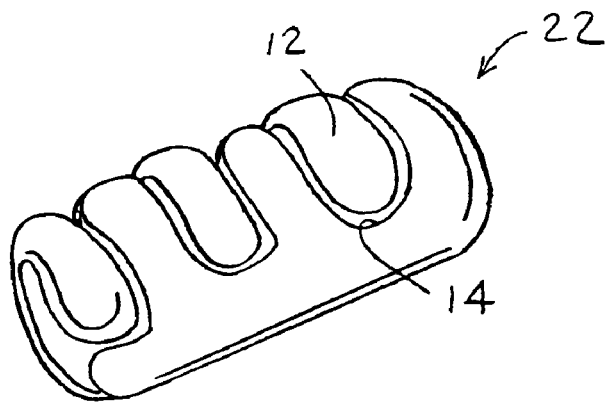
FIG. 3 is a simplified illustration of the apparatus of FIG. 1 folded/bent/rolled or otherwise shaped into a volumetric electrode assembly with enhanced volumetric coverage, in accordance with an embodiment of the present invention.

The first and second electromagnetic energy elements 10 and 16 may be flexible and bendable. As seen in FIG. 3, for example, the energy elements 10 and 16 may be folded/bent/rolled or otherwise shaped into a volumetric electrode assembly 22 with enhanced volumetric coverage than a planar electrode or needle electrode array. The possibilities of covering different geometric shapes are endless.

In accordance with an embodiment of the present invention, a sensor 24 may be disposed on either or both of the first and second electromagnetic energy elements 10 and 16. Without limitation, the sensor may be a temperature sensor (e.g., thermistor or thermocouple), a pressure sensor (e.g., strain gauge or load cell), and/or an electrical resistance sensor (e.g., resistive element in electrical connection with tissue) or any combination thereof. The electromagnetic energy elements 10 and 16 may be controlled by a controller (not shown) in communication with the sensor 24, wherein energy to the elements 10 or 16 is stopped upon sensor 24 sensing a desired level or degree of coagulation or necrosis (as interpreted by the controller which interprets the signals from the sensor 24), for example.

Either or both of the first and second electromagnetic energy elements 10 and 16 may be formed with one or more holes 26, such as for passing therethrough a fluid (e.g., medicine, cooling fluid, electrolytic fluid, etc.).

Figure 2:
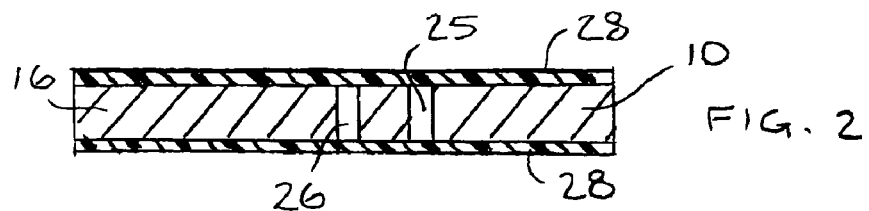
FIG. 2 is a simplified sectional illustration of the apparatus of FIG. 1, taken along lines II-II in FIG. 1.

As seen in FIG. 2, an insulating layer 28 may be placed over the first and second electromagnetic energy elements 10 and 16. The insulating layer 28 may be, without limitation, TEFLON or KAPTON. In this manner, first and second electromagnetic energy elements 10 and 16 can contact tissue even if not made of medically safe materials (e.g., copper).

Figure 4:
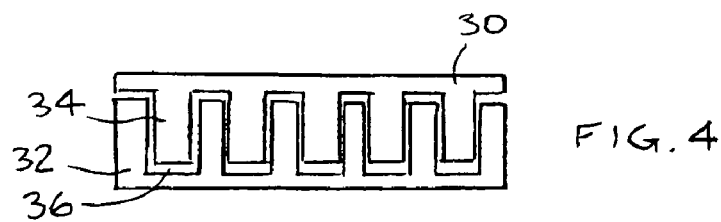
FIG. 4 is a simplified illustration of apparatus for applying energy to tissues, constructed and operative in accordance with another embodiment of the present invention.

Reference is now made to FIG. 4, which illustrates another apparatus for applying energy to tissues, constructed and operative in accordance with another embodiment of the present invention. In this non-limiting embodiment, first and second electromagnetic energy elements 30 and 32 each include interleaving protrusions and recesses which are an array of pins 34 and channels 36.

Figure 5:
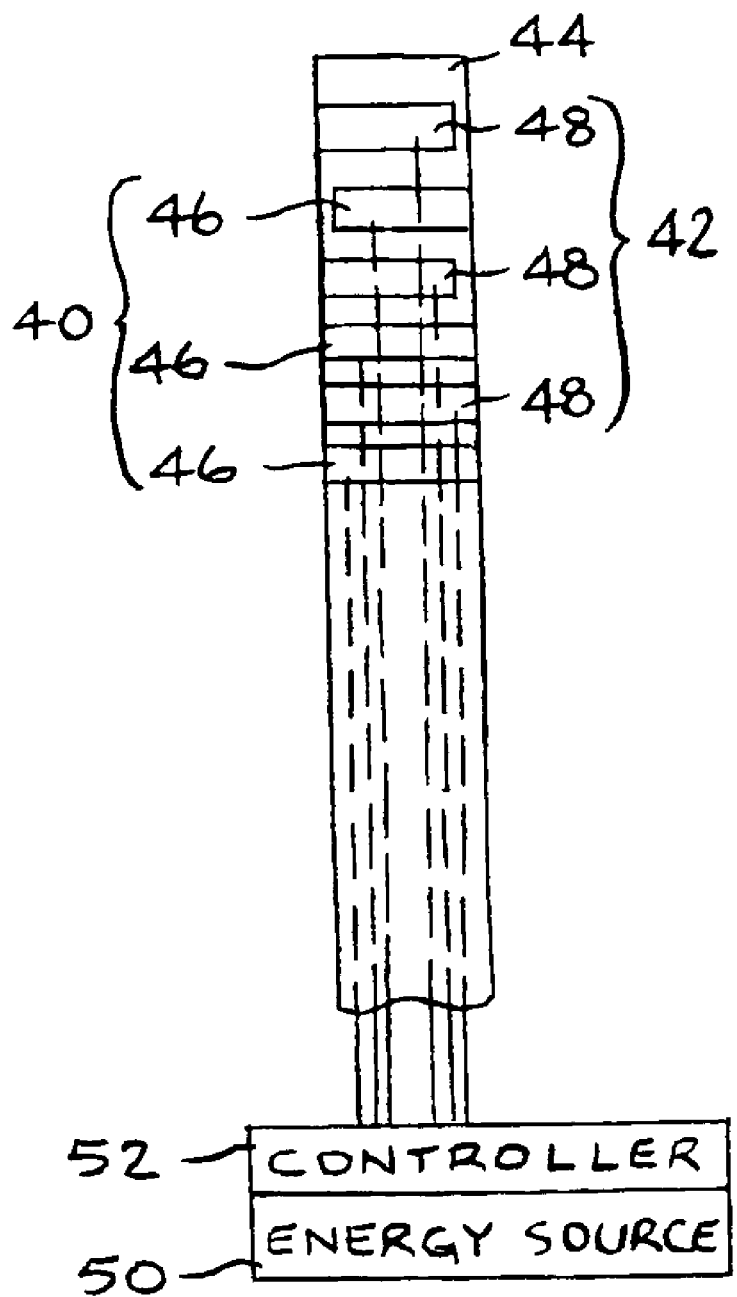
FIG. 5 is a simplified illustration of apparatus for applying energy to tissues, constructed and operative in accordance with yet another embodiment of the present invention.

Reference is now made to FIG. 5, which illustrates yet another apparatus for applying energy to tissues, constructed and operative in accordance with yet another embodiment of the present invention. In this non-limiting embodiment, first and second electromagnetic energy elements 40 and 42 include interleaving annular electrodes that partially or fully circumscribe a shaft 44. For example, the interleaving annular electrodes may be made of metal (e.g., medically safe stainless steel) which are deposited or otherwise disposed upon shaft 44, which may be made of a medically safe insulating material (e.g., latex). The interleaving annular electrodes may be grouped as odd-numbered electrodes (designated by reference numeral 46) and even-numbered electrodes (designated by reference numeral 48).

A source 50 of electromagnetic energy (e.g., RF generator) may be connected to the odd-numbered electrodes 46 and the even-numbered electrodes 48 for operating them as bipolar electrodes, as controlled by a controller 52. Different patterns and groupings of the annular electrodes may also be used. For example, the first, fourth and seventh electrodes may comprise one group, while the second, third, fifth and sixth may comprise another group. In general, each electromagnetic energy element may be formed by sub-elements operable to be electrically connected to each other, thus changing the shape of the electromagnetic energy elements.

Of course the invention is not limited to the above constructions, and other interleaving constructions are possible within the scope of the invention.

The scope of the present invention includes both combinations and subcombinations of the features described hereinabove as well as modifications and variations thereof which would occur to a person of skill in the art upon reading the foregoing description and which are not in the prior art.

What is claimed is:

1. Apparatus comprising:
a first electromagnetic energy element that comprises cantilevered protrusions that jut into recesses formed in a second electromagnetic energy element, said protrusions and said recesses interleaving with each other and being separated by a gap; and
a source of electromagnetic energy connected to said first and second electromagnetic energy elements for operating said first and second electromagnetic energy elements as bipolar electrodes capable of conducting bipolar energy through said gap, and wherein said first and second electromagnetic energy elements are flexible and said protrusions are bent into an arcuate shape to form a volumetric electrode assembly.

2. Apparatus according to claim 1, wherein said first and second electromagnetic energy elements each comprise an electrically conducting member with a serpentine surface that defines the interleaving protrusions and recesses.

3. Apparatus according to claim 1, further comprising a sensor disposed on at least one of said first and second electromagnetic energy elements.

4. Apparatus according to claim 3, wherein said sensor comprises at least one of a temperature sensor, a pressure sensor, and an electrical resistance sensor.

5. Apparatus according to claim 1, wherein at least one of said first and second electromagnetic energy elements is formed with a hole.

6. Apparatus according to claim 5, wherein said hole passes through one of said protrusions.

7. Apparatus according to claim 1, further comprising an insulating layer placed over said first and second electromagnetic energy elements.

8. Apparatus according to claim 1, wherein said first and second electromagnetic energy elements are separated by an air gap through their entire thicknesses.

\* \* \* \* \*